(12) United States Patent  (10) Patent No.: US 9,272,108 B2
Hu  (45) Date of Patent: Mar. 1, 2016

(54) OXYGEN MASK

(76) Inventor: Henry Hu, Andover, MA (US)

( * ) Notice: Subject to any disclaimer, the term of this patent is extended or adjusted under 35 U.S.C. 154(b) by 0 days.

(21) Appl. No.: 12/984,037

(22) Filed: Jan. 4, 2011

(65) Prior Publication Data

US 2012/0172740 A1 Jul. 5, 2012

Related U.S. Application Data

(60) Provisional application No. 61/335,253, filed on Jan. 4, 2009.

(51) Int. Cl.
A61B 18/02 (2006.01)
A61M 16/06 (2006.01)
A61M 16/04 (2006.01)
A61M 16/08 (2006.01)
A61M 16/10 (2006.01)

(52) U.S. Cl.
CPC ............ *A61M 16/06* (2013.01); *A61M 16/0463* (2013.01); *A61M 16/0683* (2013.01); *A61M 16/0816* (2013.01); *A61M 16/10* (2013.01); *A61M 2202/0208* (2013.01)

(58) Field of Classification Search
CPC ....................... A61M 6/06; A61M 2016/0661
USPC ...................................... 600/532; 128/206.21
See application file for complete search history.

(56) References Cited

U.S. PATENT DOCUMENTS

| 2,625,155 | A | 1/1953 | Engelder |
| 3,905,361 | A | 9/1975 | Hewson et al. |
| 4,106,505 | A | 8/1978 | Salter et al. |
| D250,131 | S | 10/1978 | Lewis et al. |
| 4,201,205 | A | 5/1980 | Bartholomew |
| 4,328,797 | A | 5/1982 | Rollins et al. |
| 4,454,881 | A | 6/1984 | Huber et al. |
| 4,470,413 | A | 9/1984 | Warncke |
| 4,719,911 | A | 1/1988 | Carrico |
| 4,794,921 | A * | 1/1989 | Lindkvist ................. 128/203.29 |
| 4,848,331 | A * | 7/1989 | Northway-Meyer .... 128/200.26 |
| 4,890,609 | A | 1/1990 | Wilson |
| 5,143,061 | A | 9/1992 | Kaimer |
| 5,431,158 | A | 7/1995 | Tirotta |
| 5,474,060 | A * | 12/1995 | Evans ...................... 128/204.22 |
| 6,196,223 | B1 | 3/2001 | Belfer et al. |
| 6,386,198 | B1 | 5/2002 | Rugless |
| 6,439,230 | B1 * | 8/2002 | Gunaratnam et al. ... 128/206.21 |
| 6,530,374 | B1 | 3/2003 | Ferraro |
| 6,736,139 | B1 | 5/2004 | Wix |
| 6,792,943 | B2 * | 9/2004 | Kumar et al. ............ 128/200.26 |
| 8,365,734 | B1 | 2/2013 | Lehman |
| 2003/0024533 | A1 | 2/2003 | Sniadach |
| 2004/0065327 | A1* | 4/2004 | Gradon et al. ........... 128/206.21 |
| 2007/0277825 | A1* | 12/2007 | Bordewick et al. ...... 128/204.23 |
| 2007/0295335 | A1* | 12/2007 | Nashed .................... 128/206.24 |
| 2008/0053449 | A1 | 3/2008 | Lindblom et al. |
| 2010/0229872 | A1 | 9/2010 | Ho |

* cited by examiner

*Primary Examiner* — Etsub Berhanu
(74) *Attorney, Agent, or Firm* — John H. Pearson, Jr.; Walter F. Dawson; Pearson & Pearson, LLC

(57) ABSTRACT

An anatomical shaped oxygen face mask with ports allows medical procedures to take place while the mask remains affixed to patient's face covering both mouth and nose. The mask is specially designed to allow the patient to ventilate spontaneously while at the same time allowing access for instruments by means of ports located at the front of the mask. One port may be used for procedures while another port can be used for suctioning of secretion and blood or for providing oxygen.

11 Claims, 4 Drawing Sheets

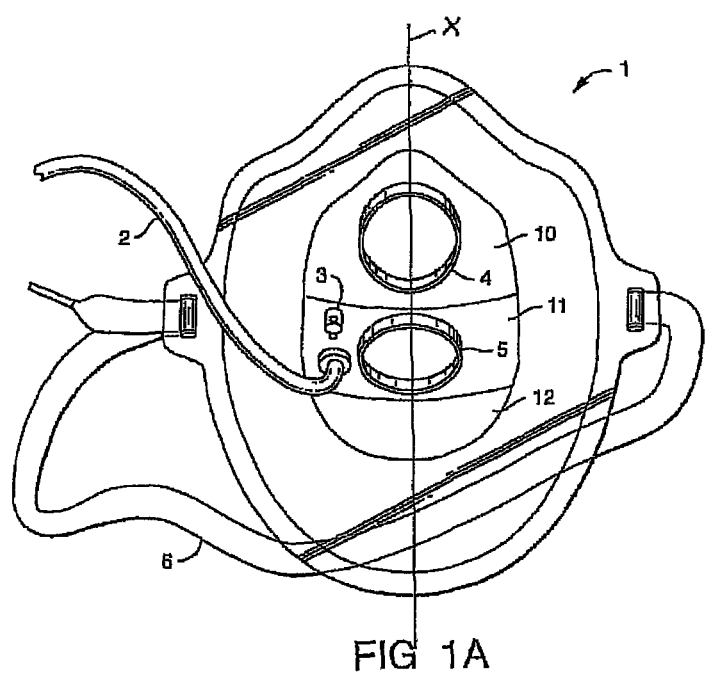
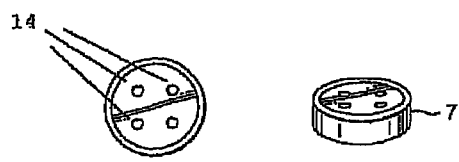
FIG. 1B  FIG. 1C

OXYGEN MASK

PROSECUTION HISTORY

This application claims priority on U.S. Provisional Application No. 61/335,253, filed on Jan. 4, 2010.

FIELD OF THE DEVICE AND METHOD

The present device and method is generally related to medical devices, more specifically the present device and method relates to an oxygen face mask capable of providing continuous oxygen to the patient, and at the same time provides access to mouth or/and nose during medical procedures.

BACKGROUND OF THE DEVICE AND METHOD

Bronchoscopy, esophagogastroduodenoscopy and transesophageal echocardiogram are widely used for diagnostic and therapeutic purposes by different specialists everyday. Patients undergoing those procedures require intravenous anesthetics to maintain deep sedation with spontaneous ventilation. Currently nasal cannula is used for this purpose. However, nasal cannula does not generally provide adequate oxygen levels, especially in the case of patients who are prone to be mouth breathers, when instruments are inserted in the mouth. Such patients often experience oxygen desaturation during this and similar procedures.

On the other hand, currently used oxygen face masks would provide oxygen retention to reach adequate oxygen level inside the mask by completely covering both mouth and nose, but such face masks do not provide access for instruments to enter through the mask into airways, trachea, the esophagus and gastrointestinal (GI) tracts.

U.S. Pat. No. 5,431,158, issued to Tirotta on Jul. 11, 1995, provide an endoscopy breathing mask having a hollow bite block to accommodate introduction of an endoscope. However, the elongated bite block significantly increases friction of the instrument and interferes with the endoscopist's performance. It doesn't allow multifunction access to mouth and nose: that is, for the introduction of several different instruments for different purposes, such as fiber optic bundles for viewing, cutters, clamps, etc., and for procedures requiring the suctioning of secretion or blood at the same time. Furthermore the bite block isn't practical for use after the procedure, when the patient is conscious, due to the patient's discomfort with oral bite block in place.

However, nothing in the design of the present device would prevent the use of a bite block if desired, and a bite block is included in an alternative embodiment.

In sum, none of the currently existing devices discloses or suggest all of the features provided and claimed by present device and method.

SUMMARY OF THE DEVICE AND METHOD

It is an objective of the presently describe device and method to efficiently provide oxygen to a patient undergoing a medical procedure involving the insertion of instruments and the like into the nose and/or mouth of the patient.

In accordance with one aspect of the device, an oxygen mask has affixed to it one or more ports, each in proximity to the mouth or nose, and each disposed along a vertical line bisecting the face, and each such port of a size sufficient to allow the passage of instruments into the nose or mouth during a medical procedure.

In accordance with a second aspect of the device one or more caps are included, each having exhalation pores, and each matingly affixable to the corresponding port.

In accordance with a third aspect of the device, means for conveying oxygen into the mask are further provided.

In accordance with a fourth aspect of the device, means for sampling carbon dioxide are also provided.

In accordance with a fifth aspect of the device, when the number of ports is two or more, and when one port is used for the insertion of instruments into the nose or mouth another port is used for suctioning of fluids off from within the mask.

In accordance with a sixth aspect of the device, the oxygen mask is transparent.

BRIEF DESCRIPTION OF THE DRAWINGS

These, and other aspects of the device and method may be understood by reference to the attached drawings, in which:

FIG. 1A depicts a perspective view of the mask.

FIG. 1B depicts a top plan view of a cap used to cover a port.

FIG. 1C depicts a perspective view of the cap of FIG. 1A

DESCRIPTION

The presently-described oxygen mask is a transparent, ergonomic, anatomically fitted device. It is disposed on the face over the chin 8 as may be seen by referring now to FIG. 4. It is shorter than the oxygen masks of the related art, extending only as high as the approximate vertical mid-point of the nose.

The mask contains ports to enable the medical practitioner to easily insert instruments into patients' airways and still allow oxygen retention.

Unlike some of the related art which provides for ports in an oxygen mask, the ports of the present device and method are disposed along a vertical line which bisects the face, so that the nose and mouth of the patient are easily accessible to the ports The two ports of this embodiment, designated as the upper port 4 and lower port 5, are provided with exhalation function caps, appearing as FIGS. 1B and 1C. These caps contain pores 14 to allow for the removal of carbon dioxide exhaled by the patient, which would otherwise interfere with normal respiration. These pores 14 are sufficiently small so that only minimal air will enter from the outside, so that the patient will be breathing a high concentration of oxygen.

Figure 2:
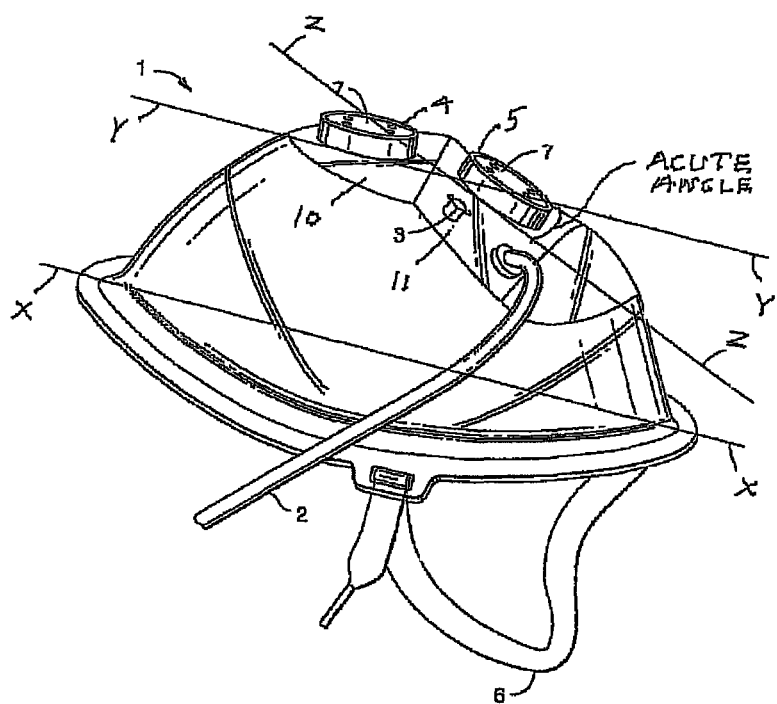
FIG. 2 depicts a right side perspective view of the oxygen mask, with the ports covered by caps.
Figure 3:
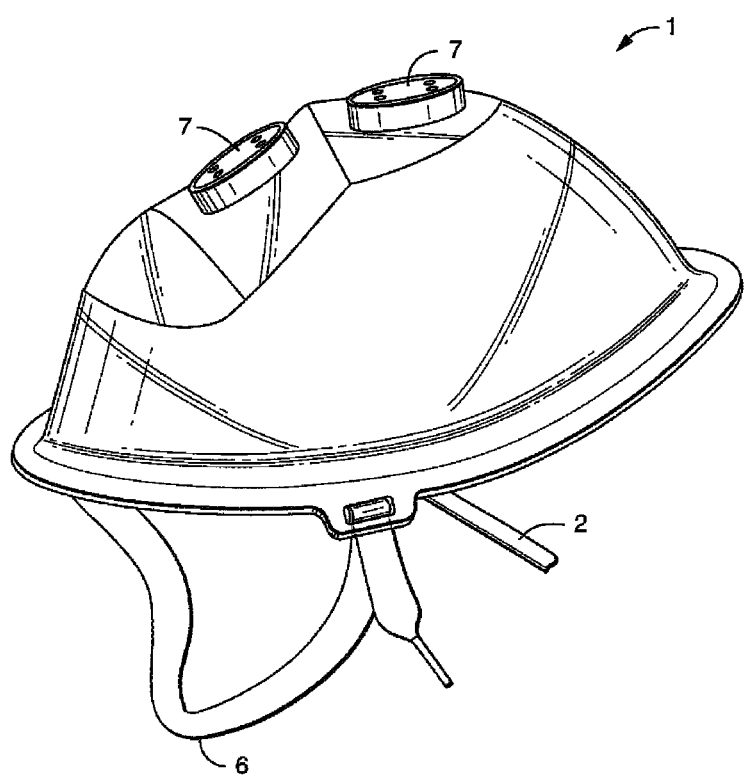
FIG. 3 depicts a left side perspective view thereof.
Figure 4:
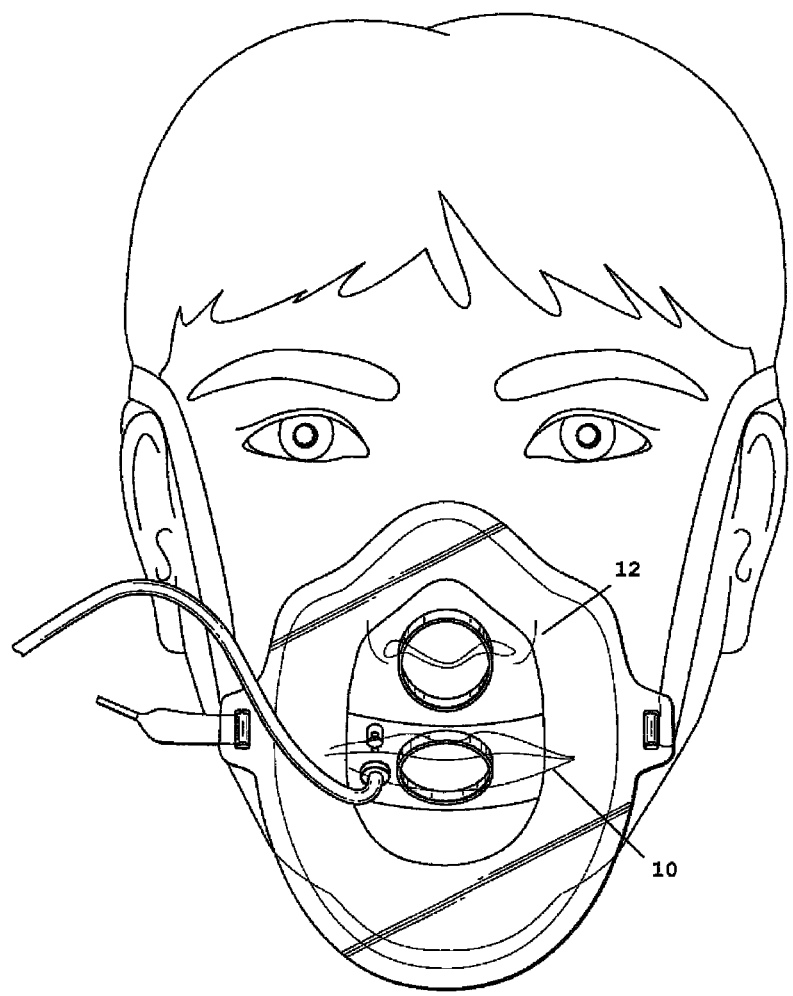
FIG. 4 depicts a front perspective view of the mask in place on the face of a patient.

Referring to FIG. 1A, FIG. 2 and FIG. 4, FIG. 2 is a right side perspective view of the oxygen mask 1, and it shows the front surface of the mask 1 having two transitional downward sloping planes 10, 11 (FIG. 1A) that depart from the overall curvature of the front surface of the mask 1. The upper port 4 is located on the first downward sloping plane 10 and lower port 5 is located on the second downward sloping plane 11 which is angled inward with respect to plane 10 toward the face of a patient wearing the mask 1 at approximately a midpoint along the front surface of mask 1. The first downward sloping plane 10 is parallel to a vertical line bisecting a face of mask 1 as shown in FIG. 2 and FIG. 4 and the second downward sloping plane 11 is angled inward at an acute angle with respect to said first transitional downward sloping plane 10 towards the face of the patient (who wears the mask) as shown in FIGS. 2 and 3. The greater this acute angle is between the first transitional downward sloping plane 10 and the second transitional downward sloping plane 11, the opening of lower port 5 becomes more directly opposite the nostrils of the patient. This mask design results in the upper port 4 being located opposite a nose tip of the patient wearing the mask 1 as shown in FIG. 4 and the lower port 5 being located approximately opposite a mouth of the patient and angled toward the nostrils of the patient to facilitate different endoscopy procedures through the mouth and nose of the patient. The immediately adjacent sloping planes 10,11 enable the ports 4,5 to be positioned to facilitate insertion of medical instruments through ports 4,5 to the mouth or nose of the patient. Typically, the upper port 4 is used to pass medical instruments to the mouth of the patient and the lower port 5 is used to pass medical instruments to the nostrils of the patient. However, for medical procedures on some patients and because of the unique structure of mask 1, the upper port 4 may be used to pass medical instruments to the nose of a patient and the lower port 5 may be used to pass instruments to the mouth of the patient when the particular procedure may be performed more easily and safely for the patient.

Alternatively, the lower port 5 can be used for passing instruments (for instance, a bronchoscope) through the patient's nose into the patient's upper airways, while, at the same time the upper port 4 is available for suctioning off secretions or blood.

The lower port 5 can also be used for fiber optic nasal intubation. Oxygen from the oxygen supply is delivered via the oxygen tubing 2 to the mask for patients to inhale, and the use of this techniques achieve adequate oxygen levels to the patient during intubation.

The presently-described device, with both caps in place, can function as a previously-used oxygen face mask, and may continue to be used after procedures are completed.

A number of medical procedures including, but not limited to bronchoscopy, esophagogastroduodenoscopy (EGD), transesophageal echocardiogram (TEE), fiber optic intubation and ENT procedures, will benefit from the presently-described surgical mask.

In use in the current embodiment, the mask is affixed to the face of the patient while oxygen is pumped into the mask through the oxygen tube 2. This is normally done after the patient is sedated, but most usually after the patient has been anesthetized.

In the case where instruments are to be introduced into the mouth of the patient, a bite block is inserted into the patient's mouth to prevent the patient from biting down on the instruments to be inserted, so as to protect both the instruments and the patient's teeth from damage, and the mask then placed on the patient's face. The instruments are then inserted into the nose or mouth of the patient, as the case may be.

The transparency of the mask facilitates the insertion of the tubes or instruments into the patient's mouth or nose.

If one of the ports is not needed in the procedure being performed, the other port is capped. The caps 7 contain exhalation pores 14 which provide for the exhalation of the patient, thereby providing for the removal of the carbon dioxide exhaled by the patient, and preventing the mask from being over-inflated by the patient's exhalent.

As noted in the attached figures, means are provided to attach a carbon-dioxide sampling tube to the mask by means of the coupling 3 placed to the side of the mask in a position so as not to interfere with the insertion of instruments through the ports.

As may be seen by reference to FIG. 4, the upper part of the mask is affixed to the patient's face about half-way down the patient's nose 12. This positioning prevents the mask from inadvertently damaging the patient's eyes during the procedures. The upper port 4 is in proximity to the bottom of the patient's nose. The lower port 5 is in proximity to the patient's mouth 10.

Instruments for insertion into the patient's mouth would be introduced into upper port 4, and disposed downward. Conversely, instruments to be inserted into the patient's nose would be introduced through the lower port 5, and disposed at an upper angle.

Although the device and method has been described in conjunction with the foregoing specific embodiment, many alternatives, variations, and modifications will be apparent to those of ordinary skill in the art. Such alternatives, variations, and modifications are intended to fall within the scope of the appended claims.

The invention claimed is:

1. A multifunction oxygen mask for attaching to a face of a patient for enabling medical procedures to be performed comprising:
   at least two instrument ports corresponding to an upper port and a lower port;
   said ports being usable for medical instrument access and configured to be disposed along a vertical line bisecting a face of said mask, said mask configured to extend from approximately a midpoint of a patient's nose to over a chin of said patient;
   a center area of said face of said mask having said upper port located on a first transitional downward sloping plane parallel to said vertical line and said lower port being located on a second transitional downward sloping plane which is angled inward at an acute angle with respect to said first transitional downward sloping plane toward said face of said patient and located at approximately a midpoint along said face of said mask immediately below said upper port, wherein when attached to the face of the patient, said upper port is located opposite a nose tip of said patient and said lower port is located opposite a mouth of said patient and angled towards nostrils of said patient;
   each of said at least two instrument ports having an unblocked and nonfenestrated opening cylindrically protruding from an outer surface of said mask and being of a sufficient size and aligned to pass medical instruments into the mask during a medical procedure;
   said upper port on said first transitional downward sloping plane and said lower port on said second transitional downward sloping plane being angled toward said nostrils of said patient when wearing said mask and located in an arrangement wherein a first of said medical instruments can be inserted through said upper port into either said nostrils or mouth of said patient and a second of said medical instruments can be inserted through said lower port into either said nostrils or mouth of said patient; and
   said medical instruments including one of a group consisting of an endoscope, a TEE Probe, and a flexible fiberoptic laryngoscope or bronchoscope.

2. The oxygen mask of claim 1, further comprising one or more caps, each cap comprising a multiplicity of exhalation pores, and each cap matingly affixable to a corresponding port.

3. The oxygen mask of claim 2, further comprising tubular means for conveying oxygen into the mask.

4. The oxygen mask of claim 3, further comprising tubular means for sampling carbon dioxide.

5. The oxygen mask of claim 1, wherein the oxygen mask is transparent to facilitate said insertion of said medical instruments or a tube.

6. The oxygen mask as recited in claim 1 wherein said mask comprises a cap on each port enabling said mask to function as an oxygen face mask.

7. A multifunction oxygen mask for attaching to a face of a patient for enabling medical procedures to be performed comprising:
   at least two instrument ports corresponding to an upper port and a lower port;
   said ports being usable for medical instrument access and configured to be disposed along a vertical line bisecting a face of said mask, said mask configured to extend from approximately a midpoint of a patient's nose to over a chin of said patient;
   a center area of said face of said mask having said upper port located on a first transitional downward sloping plane parallel to said vertical line and said lower port being located on a second transitional downward sloping plane which is angled inward at an acute angle with respect to said first transitional downward sloping plane toward said face of said patient and located at approximately a midpoint along said face of said mask immediately below said upper port, wherein when attached to the face of the patient, said upper port is located opposite a nose tip of said patient and said lower port is located opposite a mouth of said patient and angled towards nostrils of said patient;
   each of said at least two instrument ports having an unblocked and nonfenestrated opening cylindrically protruding from an outer surface of said mask and being of a sufficient size and aligned to pass medical instruments into the mask during a medical procedure;
   said upper port on said first transitional downward sloping plane located opposite said patient's nose and said lower port on said second transitional downward sloping plane located opposite said patient's mouth and being angled toward said nostrils of said patient when wearing said mask and located in an arrangement wherein a first of said medical instruments can be inserted through said upper port into said mouth of said patient and a second of said medical instruments can be inserted through said lower port into said nostrils of said patient; and
   said medical instruments including one of a group consisting of an endoscope, a TEE Probe, and a flexible fiberoptic laryngoscope or bronchoscope.

8. The oxygen mask as recited in claim 7, further comprising tubular means for conveying oxygen into the mask.

9. The oxygen mask as recited in claim 7, wherein the oxygen mask is transparent to facilitate said insertion of said medical instruments or a tube.

10. The oxygen mask as recited in claim 7 wherein said mask comprises a cap on each port enabling said mask to function as an oxygen face mask.

11. A method of using a multifunction oxygen mask attached to a face of a patient for enabling medical procedures to be performed comprising the steps of:
   providing on said mask at least two instrument ports corresponding to an upper port and a lower port;
   using said ports for medical instrument access;
   configuring said ports to be disposed along a vertical line bisecting a face of said mask;
   forming a length of said mask to extend from approximately a midpoint of a patient's nose to over a chin of said patient wearing said mask;
   locating said upper port in a center area of said face of said mask on a first transitional downward sloping plane parallel to said vertical line;
   locating said lower port on a second transitional downward sloping plane which is angled inward at an acute angle with respect to said first transitional downward sloping plane toward said face of said patient and located at approximately a midpoint along said face of said mask immediately below said upper port, wherein when attached to the face of the patient said upper port is located opposite a nose tip of said patient and said lower port is located opposite a mouth of said patient and angled towards nostrils of said patient;
   attaching said mask to the face of the patient; and
   using each of said at least two instrument ports, having an unblocked and nonfenestrated opening cylindrically protruding from an outer surface of said mask, to pass medical instruments into the mask during a medical procedure;
   wherein a first of said medical instruments is inserted through said upper port into said mouth of said patient and a second of said medical instruments is inserted through said lower port into said nostrils of said patient; and
   wherein the medical instruments include one of a group consisting of an endoscope, a TEE probe, and a flexible fiberoptic laryngoscope or bronchosope.

* * * * *